(12) United States Patent
Yildirim et al.

(10) Patent No.: US 11,439,503 B2
(45) Date of Patent: Sep. 13, 2022

(54) IMPLANTABLE VALVE PROSTHESIS (71) Applicant: Universitaetsklinikum Hamburg-Eppendorf, Hamburg (DE)

(72) Inventors: Yalin Yildirim, Hamburg (DE); Simon Pecha, Hamburg (DE); Hermann Reichenspurner, Hamburg (DE)

(73) Assignee: Universitaetsklinikum Hamburg-Eppendorf, Hamburg (DE)

( * ) Notice: Subject to any disclaimer, the term of this patent is extended or adjusted under 35 U.S.C. 154(b) by 0 days.

(21) Appl. No.: 16/644,664

(22) PCT Filed: Sep. 6, 2018

(86) PCT No.: PCT/DE2018/200084
§ 371 (c)(1),
(2) Date: Mar. 5, 2020

(87) PCT Pub. No.: WO2019/052610
PCT Pub. Date: Mar. 21, 2019

(65) Prior Publication Data
US 2020/0397569 A1    Dec. 24, 2020

(30) Foreign Application Priority Data
Sep. 13, 2017  (DE) .................... 10 2017 121 143.8

(51) Int. Cl.
*A61F 2/24*     (2006.01)
*A61F 2/06*     (2013.01)
*A61F 2/07*     (2013.01)

(52) U.S. Cl.
CPC .............. *A61F 2/2418* (2013.01); *A61F 2/06* (2013.01); *A61F 2/07* (2013.01); *A61F 2/2412* (2013.01);
(Continued)

(58) Field of Classification Search
CPC .... A61F 2/07; A61F 2002/065; A61F 2/2418; A61F 2/2475; A61F 2/2476; A61F 2/2412; A61F 2002/068; A61F 2/06
See application file for complete search history.

(56) References Cited

U.S. PATENT DOCUMENTS 5,258,023 A  11/1993  Reger
5,669,924 A   9/1997  Shaknovich
(Continued)

FOREIGN PATENT DOCUMENTS

EP    0830109 A1    3/1998
EP    1472991 A2   11/2004
(Continued)

OTHER PUBLICATIONS

Jamieson, W.R.E., et al. "Clinical and Hemodynamic Performance of the Sorin Mitroflow Pericardial Bioprosthesis", Published online: Dec. 9, 2011, Publisher: InTech, Chapter from the book Aortic Valve, Clinical and Hemodynamic Performance of the Sorin Mitroflow Pericardial Bioprosthesis, Aortic Valve, Prof. Chen Ying-Fu (Ed.), ISBN: 978-953-307-561-7, InTech, Available from: http://www.intechopen.com/books/aortic-valve/clinical-and-hemodynamic-performance-of-the-sorin-mitroflow-pericardial-bioprosthesis.
(Continued)

*Primary Examiner* — Suba Ganesan
(74) *Attorney, Agent, or Firm* — Patent Central LLC; Stephan A. Pendorf (57) ABSTRACT

An implantable valve prosthesis for preventing blood reflux from a cardiac atrium into a vein opening into the atrium, with a generally tubular stent (2), also a flexible tube (3) that can be closed by collapsing the tube (3) and which is arranged at least in a partial area of a second end section (9) of the stent (2) on the outer peripheral surface. The second end opening (11) of the flexible tube (3) is open in the pressureless state. As a result of this valve design, during a
(Continued)

physiological flow out of the pulmonary vein in the direction of the left atrium or out of the caval vein in the direction of the right atrium, there is no rise or an only insubstantial rise in the resistance to flow.

16 Claims, 8 Drawing Sheets

(52) U.S. Cl.
CPC ........... *A61F 2/2475* (2013.01); *A61F 2/2476* (2020.05); *A61F 2002/065* (2013.01); *A61F 2002/068* (2013.01)

(56) References Cited

U.S. PATENT DOCUMENTS

| | | | |
|---|---|---|---|
| 5,855,597 | A | 1/1999 | Jayaraman |
| 6,168,614 | B1 | 1/2001 | Andersen et al. |
| 7,641,686 | B2 | 1/2010 | Lashinski et al. |
| 7,771,467 | B2 | 8/2010 | Svensson |
| 2002/0107565 | A1* | 8/2002 | Greenhalgh ......... A61F 2/2418 623/1.24 |
| 2003/0060894 | A1* | 3/2003 | Dua .................... A61F 2/04 623/23.68 |
| 2004/0102855 | A1 | 5/2004 | Shank |
| 2004/0210306 | A1* | 10/2004 | Quijano ............... A61F 2/2418 623/2.17 |
| 2006/0111773 | A1 | 5/2006 | Rittgers et al. |
| 2006/0212111 | A1* | 9/2006 | Case .................... A61F 2/2475 623/1.24 |
| 2012/0053676 | A1* | 3/2012 | Ku ....................... A61F 2/2412 623/1.26 |
| 2015/0282958 | A1* | 10/2015 | Centola ................ A61F 2/07 623/2.15 |
| 2015/0359628 | A1* | 12/2015 | Keränen .............. A61F 2/2466 623/2.18 |
| 2018/0318071 | A1* | 11/2018 | Lozonschi ........... A61F 2/2412 |

FOREIGN PATENT DOCUMENTS

| | | |
|---|---|---|
| EP | 2568925 B1 | 8/2017 |
| FR | 2788217 A1 | 7/2000 |
| WO | 2009153768 A1 | 12/2009 |
| WO | 2014165010 A1 | 10/2014 |

OTHER PUBLICATIONS

Jamieson, W.R.E., et al.: "Mitroflow aortic pericardial bioprosthesis—clinical performance", European Journal of Cardio-Thoracic Surgery 36 (2009), pp. 818-824.

Kheradvar, A. et al.: "Emerging Trends in Heart Valve Engineering: Part II. Novel and Standard Technologies for Aortic Valve Replacement", Biomedical Engineering Society, DOI: 10.1007/s10439-014-1191.5, Published online: Dec. 2, 2014.

Lin, P.H., et al.: "Evaluation of thrombolysis in a porcine model of chronic deep venous thrombosis: An endovascular model", Journal of Vascular Surgery, vol. 33, No. 3, pp. 621-627, Mar. 2001.

Ratschiller, T. "Trikuspidalklappenrekonstruktion mit dem Contour 3D Ring: klinische und funktionelle Ergebnisse", dissertation, Feb. 19, 2014, Technical University Munich.

Russel, C. "Heart Valves: A Fluid Dynamics Perspective", University of British Columbia MECH 410L—Mechanics of Biofluids, Term Project Report, Apr. 25, 2008.

Vaquerizo, B., et al.: "Percutaneous Transcatheter Mitral Valve Replacement: Patent-specific Three-dimensional Computer-based Heart Model and Prototyping", Rev Esp Cardiol, 2015: 68 (12), pp. 1165-1173, Sociedad Espanola de Cardiologia, Published by Elsevier Espana, S.L.U.

International Search Report dated Feb. 25, 2019, in International Application No. PCT/DE2018/200084.

\* cited by examiner

IMPLANTABLE VALVE PROSTHESIS

The invention relates to an implantable valve prosthesis, in particular for the prevention of blood reflux from a cardiac atrium to a vein that opens into the cardiac atrium.

The mitral valve acts to prevent the reflux of blood from the left ventricle into the left cardiac atrium during systole. However, mitral valve insufficiency is highly prevalent. The main clinical symptom of severe mitral valve insufficiency is dyspnoea, which is caused by congestion of blood in the lungs. In addition to surgical mitral valve reconstruction or replacement, interventional procedures are available. Examples of mitral valve replacements which have been described in the prior art are mitral valve prostheses (see, for example, U.S. Pat. Nos. 5,258,023 A, 7,641,686 B2, Vaquerizo et al. 2015, Percutaneous Transcatheter Mitral Valve Replacement: Patient-specific Three-dimensional Computer-based Heart Model and Prototyping, Rev. Esp. Cardiol. 68, 1165-1173, doi: 10.1016/j.rec.2015.08.005; Jamieson et al. 2009, Mitroflow aortic pericardial bioprosthesis—clinical performance, Eur J Cardiothorac Surg 36, 818-824, doi: 10.1016/j.ejcts.2009.05.020).

The tricuspid valve operates to prevent the reflux of blood from the right ventricle into the right cardiac atrium during systole. In patients with a compromised right ventricular heart function, tricuspid valve insufficiency constitutes a frequent clinical problem. Apart from surgical tricuspid valve reconstruction or replacement, until now, no clinically established interventional procedures have been available. The main clinical symptoms of severe tricuspid insufficiency are congestion of blood in the liver and kidneys, ascites and oedema. In the long term, this causes the development of liver and kidney dysfunction.

The known prostheses and procedures, however, are not promising for all patients since, because of the variety of anatomical as well as morphological circumstances involving the valves such as, for example, severe dilation of the mitral or tricuspid ring or other anatomical characteristics, interventional procedures for repairing the mitral valve or tricuspid valve have reached their limits.

Thus, the objective of the present invention is to provide an alternative to the means available until now for the treatment of a mitral valve or tricuspid valve insufficiency which in particular can be employed independently of the anatomy and morphology of the mitral and tricuspid valves.

The objective is achieved by means of an implantable valve prosthesis, in particular for preventing blood reflux from a cardiac atrium into a vein opening into the atrium, comprising
- a generally tubular stent which may be branched or unbranched and which comprises at least a first end section with a first end opening and a second end section with a second end opening, and
- a flexible tube which may be branched or unbranched and which has at least a first end section with a first end opening and a second end section with a second end opening which can be closed by collapsing the tube and which is disposed at least in a sub-region of the second end section of the stent on the outer peripheral surface thereof in a manner such that the second end section of the tube with its second end opening protrudes beyond the second end opening of the stent, wherein the second end opening of the tube is open in the unpressurized state.

The valve prosthesis in accordance with the invention is interventionally implantable and particularly suitable for preventing or minimizing a reflux of blood from the left atrium through the pulmonary veins to the lungs or for preventing or minimizing a reflux of blood from the right atrium into the caval veins, and thus for use in a symptomatic therapy of mitral valve insufficiency or tricuspid valve insufficiency.

The valve prosthesis is configured in a manner such that it can be anchored interventionally in a pulmonary vein or caval vein with one end while its other end protrudes freely into the associated atrium. In this regard, the valve prosthesis is configured in a manner such that in the neutral state, i.e. when the tube that protrudes into the atrium is not pressurized by an external overpressure or internal underpressure, the valve is open, while when pressure is applied from outside or an underpressure is applied from inside, the valve is closed by collapse of the tube end. An application of an external overpressure or internal underpressure to the tube end may, for example, be a consequence of a reflux of blood from the contracting left ventricle into the left atrium via an insufficiently tight mitral valve or a reflux of blood from the contracting right ventricle into the right atrium via an insufficiently tight tricuspid valve.

As a result of this valve design, during a physiological flow out of the pulmonary vein in the direction of the left atrium or out of the caval vein in the direction of the right atrium, there is no rise or an only insubstantial rise in the resistance to flow. Compared with known heart valves which are closed in the normal position and only open after a resistance has been overcome, the resistance to flow with the valve in accordance with the invention is almost negligible. In the case of a non-physiological reflux out of the atrium in the direction of the veins opening into the atrium, an underpressure caused by it in the interior of the tube end protruding into the atrium or an overpressure in the atrium leads to a collapse of the tube valve, and thus to a competent closure of the valve. Thus, reverse flow into the lungs and the associated dyspnoea as the major symptom of mitral insufficiency or a reverse flow into the caval veins and thus a consequent congestion of blood in the liver and kidneys is prevented, without the valve causing a substantial flow barrier for the physiological blood flow. In this manner, patients for whom a surgical therapy would be too risky and for whom a known conventional interventional procedure is not possible for anatomical reasons are offered a symptomatic therapy for mitral or tricuspid insufficiency. This is completely independent of the pathology and the anatomical characteristics of the mitral or tricuspid valve.

The expression "in order to prevent blood reflux from a cardiac atrium into a vein opening into the atrium" in the context of the implantable valve prosthesis in accordance with the invention refers to the ability of the valve prosthesis to prevent blood reflux from the left cardiac atrium into a pulmonary vein or from the right cardiac atrium into a caval vein.

The expression "interventionally implantable" in the context of the valve prosthesis in accordance with the invention means that the valve prosthesis can be implanted in a minimally invasive manner by means of a vessel catheter.

The term "stent" should be understood to mean an implantable support or stiffening device for opening vessels or hollow organs or keeping them open. They consist of biocompatible material, for example metal or plastic. As an example, it could be a generally tubular structure formed from a metal and/or plastic fibre screen or mesh.

The term "generally tubular stent" should be understood to mean a stent which is generally tubular in configuration. As an example, the stent may be configured as a generally hollow cylindrical tube, wherein the cross section may be round or elliptical. The term "branched stent" should be understood to mean a stent which has at least one fork. As an example, the stent may be Y-shaped, so that one tube is divided into two tubes at a fork. Branched, for example Y-shaped stents, are already known in principle and have been described, for example, in EP 0 830 109 B1.

When a "stent opening" or "end opening of a stent" or an "open stent end" is mentioned here, this clearly does not refer to an opening between wires of the wire mesh forming the stent wall or stent sheath, but refers to an opening which is disposed at the end of a stent section and which is surrounded by the stent wall.

The term "flexible tube" as used here should be understood to mean that it is not rigid in configuration, but is easily pliable. In particular, this term should be understood to mean a tube which is collapsible, i.e. which collapses or is compressed under pressurized conditions which arise under physiological conditions in the left cardiac atrium during systole, in particular at the end of the contraction phase or at the start and during the outflow phase (ejection phase) of ventricle systole, so that the tube is essentially closed under these conditions. The term "physiological" here also encompasses conditions which may arise under pathological circumstances, for example in the case of mitral valve insufficiency or tricuspid valve insufficiency in the human or animal body. The term "branched tube" as used here should be understood to mean a tube which is divided or forked into separate tubular sections, for example a Y-shaped tube.

The term "collapse" with respect to an end section of the flexible tube describes the squashing together, inpouching, invagination or compression of the tube in this section, so that the tube wall is drawn or pressed towards the interior of the tube and regions of the inner wall of the tube lie on one another and reversibly close the tube. The expression wherein "the second end opening of the tube can be closed by collapsing it" means that flow of blood through it from the second end opening of the tube to the first end opening of the tube can essentially be prevented by constricting the tube cross section in the tube section between the first and second end openings. This may encompass a constriction of the cross section of the second end opening itself, but this is not necessary, in particular in the case of the embodiments described in more detail below in which the end opening has a reinforcing element.

The expression in which "the second end opening of the tube is open in the unpressurized state" means that the second end section of the tube under normal conditions with no pressure difference between the interior of the tube and the exterior of the tube is not in a collapsed state and the second end opening is open and liquid can pass through it. An unpressurized state, i.e. a state with no pressure difference between the interior and exterior of the tube, will occasionally be termed the "neutral state" here.

The term "mitral valve insufficiency" (also termed "mitral insufficiency", MI) should be understood to mean a heart valve defect in which the function of the mitral valve (also termed the bicuspid valve) of the heart, which is disposed between the left atrium and the left chamber (ventricle) of the heart and which in the functional state prevents a systolic reflux of blood from the left chamber into the left atrium, has been compromised, i.e. cannot close or does not seal, so that during the outflow phase of ventricle systole, a reflux of blood occurs from the left ventricle into the left atrium.

The term "tricuspid valve insufficiency" (also termed "tricuspid insufficiency", TI) should be understood to mean a heart valve defect in which the function of the tricuspid valve of the heart, which is disposed between the right atrium and the right chamber (ventricle) of the heart and which in the functional state prevents a systolic reflux of blood from the right chamber into the right atrium, has been compromised, i.e. cannot close or does not seal, so that during the outflow phase of ventricle systole, a reflux of blood occurs from the right ventricle into the right atrium.

The term "pulmonary veins" or "veins of the lung" refers to the venae pulmonales, i.e. blood vessels which transport oxygen-rich blood from the lung to the left atrium of the heart. In human beings, as a rule, four pulmonary veins (lower and upper right pulmonary vein as well as lower and upper left pulmonary vein), open separately into the left atrium.

The term "caval vein" refers to the venae cavae, i.e. blood vessels which transport venous blood from the body to the right cardiac atrium. As a rule, a human being has two caval veins, the upper caval vein (vena cava superior) and the lower caval vein (vena cava inferior).

The valve prosthesis in accordance with the invention is configured in a manner such that the tube end protruding beyond the stent collapses in the implanted state and is thus closed while the pressure in the atrium increases during systole. Keeping the tube open during the non-systolic phases of the cardiac cycle, in particular during the filling phase (diastole), can be ensured either by an appropriate choice of the tube material and/or of the wall thickness and/or by using suitable support elements. The tube has a sufficient flexibility/elasticity to open through the passive flow out of the lung into the atrium at the start of diastole. When the pressure in the atrium increases at the beginning of systole, the valve closes because the tube collapses, closing the end opening.

Implantation of the stent may be carried out in a manner which is known in the prior art, for example by means of a balloon catheter. In this regard, the initially collapsed stent is brought by means of the catheter to the desired location, for example a pulmonary vein opening or caval vein opening into the associated atrium, and is deployed there and then anchored. Alternatively, the valve may consist of a self-expanding material (for example a nickel-titanium alloy, Nitinol) which, after releasing the stent and in contact with the blood stream, expands to the intended size. The principles of the self-expanding valve are known to the person skilled in the art.

In a preferred embodiment of the valve prosthesis in accordance with the invention, it comprises at least one wire- or ligature-shaped stabilization element fastened to the stent or integral with the stent, wherein the stabilization element protrudes beyond the second end opening of the stent and in this manner supports the portion of the tube that protrudes beyond the second end opening of the stent in a manner such that the second end opening of the tube is open in the unpressurized condition, and when pressurized cannot gain ingress into the second end opening of the stent. In this embodiment, a wire- or ligature-shaped stabilization element extends from the end of the stent or beyond the stent end in the direction of the tube end and supports the tube from within, so that a collapse, for example invagination, of the protruding tube portion into the interior or the stent, is prevented in the neutral state. Furthermore, the wire- or ligature-shaped stabilization element also prevents invagination of the tube end into the stent in the case of an external overpressure or internal underpressure, in particular when the valve closes. This therefore prevents the portion of the tube which protrudes beyond the second end opening of the stent from being pressed or sucked back inside the stent. The stabilization element advantageously extends up to the tube end.

Particularly preferably, at least two opposing wire- or ligature-shaped stabilization elements are provided which are opposite each other and support the tube from inside. In this embodiment, collapse of the tube is essentially only possible by an inward movement of the wall regions of the tube lying between the stabilization elements. It has been shown that this embodiment functions particularly reliably and prevents an inadvertent collapse of the tubular valve portion.

As described above, the at least one wire- or ligature-shaped stabilization element also acts to prevent an invagination of the tube back into the stent, for example in an underpressure situation. Alternatively or in addition, however, to this end, the tube may widen in cross section towards its second end opening and/or may be provided in its second end section with an annular reinforcing element fastened to the outside of the tube. The internal cross section of the annular reinforcing element preferably corresponds to at least the internal cross section of the second end opening of the stent, so that penetration of the tube with its second end opening into the stent is not possible. By means of the widening towards the second end opening, because the tube cross section has been enlarged, the flow resistance is also further reduced. The annular reinforcing element stiffens the tube in its second end section, for example in the region of its second end opening, and ensures that the tube cannot be withdrawn into the stent. In this embodiment, the length of the tube section between the second stent end and the annular reinforcing element is selected in a manner such that the tube can close completely in this section. The annular reinforcing element may be designed both as embodiments with a widening of the cross section of the tube towards the second end opening as well as embodiments without such a widening of the cross section. In the case of embodiments with widening of the cross section, the internal cross section of the annular reinforcing element is larger than the internal cross section of the second end opening of the stent.

The implantable valve prosthesis in accordance with the invention is preferably configured in a manner such that when the valve prosthesis is completely closed, a coaptation length L of at least 1 cm, preferably at least 1.2 cm, 1.3 cm or 1.5 cm is produced. The term "coaptation length" should be understood to mean the length of the region of the tube in the longitudinal direction of the valve prosthesis, i.e. in the direction of flow of the blood flowing through the valve prosthesis, over which the opposing tube portions overlap to a maximum extent when the valve prosthesis is closed. The desired coaptation length may, for example, be matched to a suitable tube length which is selected for the respective valve design.

In one embodiment of the invention, which is particularly suitable for preventing blood reflux from the right cardiac atrium into a caval vein, two implantable valve prostheses as described above are connected together to form one valve prosthesis. In this embodiment, the implantable valve prosthesis in accordance with the invention comprises a first and a second implantable valve prosthesis, as described above, wherein the first and second implantable valve prostheses are disposed opposite one another in a manner such that their second tube end openings are facing each other, the second tube end openings of the first and second implantable valve prostheses are spaced from each other, the first and second implantable valve prostheses respectively have a wire- or ligature-shaped stabilization element fastened to the stent or integrally formed with the stent which extends beyond the tube end openings of the first and second implantable valve prostheses, and the first and second implantable valve prostheses are connected together by means of the at least one wire- or ligature-shaped stabilization element.

In this embodiment, two implantable valve prostheses are coupled together via the at least one wire- or ligature-shaped stabilization element, so that their second tube end openings are orientated towards each other. The positional stabilization of the valve prosthesis is increased in this embodiment. Because the tube end openings are spaced from each other, in the open state of the valve, i.e. during diastole, blood can get between the second tube end openings into the atrium. This embodiment of the implantable valve prosthesis can be implanted with the first end section of the first valve prosthesis in the upper caval vein and with the first end section of the second valve prosthesis in the lower caval vein. The valve prosthesis has a sufficient flexibility to adjust to various anatomical characteristics. The tube lengths and the separation with respect to each other may be adapted such that a reliable closure of the valve occurs during systole. In this embodiment as well, for example, two wire- or ligature-shaped stabilization elements may be provided which lie opposite each other or even may be offset with respect to each other only in the peripheral direction.

In a particularly preferred embodiment of the implantable valve prosthesis in accordance with the invention, the stent and the tube are unbranched and generally configured as hollow cylinders. This embodiment is particularly easy to produce. The stent is generally configured as a hollow cylinder and its first open end may, for example, be introduced into a pulmonary vein or caval vein and anchored there. The tube, which is also generally configured as a hollow cylinder, may be attached to the section with the second open end, which in turn protrudes with its second end beyond the second stent end and into the atrium.

In an alternative embodiment of the implantable valve prosthesis in accordance with the invention, the stent and/or the tube are branched and generally Y-shaped in configuration. In one embodiment, the stent and the tube are Y-shaped in configuration. This embodiment may, for example, be disposed with two of its stent ends in the atrial openings of the upper and lower left, in the upper and lower right pulmonary veins or the upper and lower caval vein, while the third stent end has the protruding tube end. In this manner, two pulmonary veins or the caval veins could be provided with just one valve prosthesis. The cross section of the stent section carrying the protruding tube end can be widened together with the appropriate tube section in a suitable manner such that a limitation to the flow of the blood that passes through is avoided. In a further embodiment, only the tube is Y-shaped in configuration, while two tubular stents are introduced into two of the tube ends.

The tube may consist of a suitable biocompatible material, for example a plastic material, or of body tissue, preferably human or animal body tissue. Suitable tube materials are known to the person skilled in the art.

The stent consists of a suitable biocompatible material, for example a suitable metal, for example titanium steel or Nitinol, or plastic, for example polytetrafluoroethylene (PTFE) or polyether ether ketone (PEEK). Suitable stent materials are known to the person skilled in the art.

The tube may be disposed over the entire surface of the stent, i.e. the stent may be covered by the tube in the region of its entire outer peripheral surface, so that the tube is also provided in the region at which the stent is anchored in a vein. However, the stent may also be kept free from the tube in the regions which are provided to anchor it in a vein, so that the implantable stent has direct contact with the inner wall of a vein. The latter has the advantage that the reduction in the internal vessel cross section is as small as possible, and hence the hindrance to flow is as small as possible. The tube may be fastened to the stent in a suitable manner, for example by permanent sutures or adhesion.

The implantable valve prosthesis in accordance with the invention may have one or more fastening elements, for example formed from wire, by means of which the valve prosthesis can be additionally anchored in the body, for example using surgical suture material. As an example, a wire-shaped fastening element may be fed via an implantation vein (e.g. vena subclavia) and be fixed with surgical suture material. In this manner, the implantable valve prosthesis could, for example, be fastened extravasally.

The invention will now be described with the aid of the accompanying figures as well as with the aid of an exemplary embodiment, given purely for the purposes of illustration.

Figure 1:
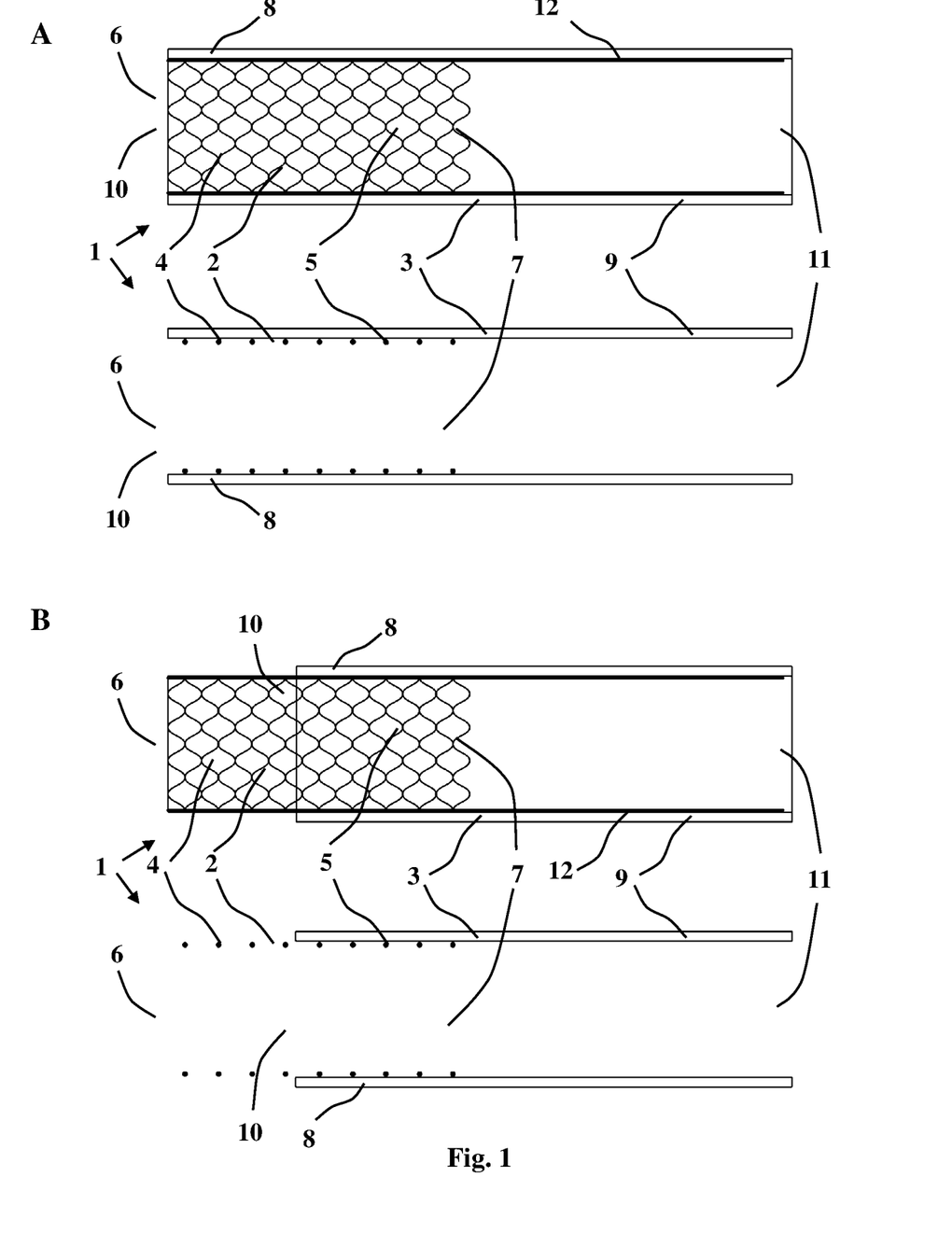
FIG. 1: two embodiments (A, B) of the valve prosthesis in accordance with the invention in side views (top) and sectional views (bottom), in which the stent is completely (A) or only partially (B) covered by the tube.

FIG. 1 shows two preferred embodiments of a valve prosthesis in accordance with the invention 1. In the upper part of the figures is a respective side view; the lower part shows a sectional view. The sectional view shows a section which is not at the level of the wire- or ligature-shaped stabilization elements 12, which in this embodiment are opposite each other (see also FIG. 2). The embodiments shown in FIGS. 1A, B of the valve prosthesis 1 in accordance with the invention are generally configured as hollow cylinders. A stent 2, which is generally in the shape of a hollow cylinder and which may be formed from a titanium steel mesh, has a first end section 4 with a first end opening 6 and a second end section 5 with a second end opening 7 which is opposite to the first end opening 6. A flexible tube 3, which is also a hollow cylinder, which may be a mesh tube, and which has a first end section 8 with a first end opening 10 and a second end section 9 with a second end opening 11, is disposed on the outer peripheral surface of the stent 2. The tube 3 in the embodiment shown in FIG. 1A is drawn completely via its first end section 8 over the stent 2 and is flush with the first end opening 6 of the stent 2. In the embodiment shown in FIG. 1B, at least a portion of the first end section 4 of the stent 2 is exposed, i.e. not covered by the tube 3. The first end section 4 of the stent 2 is thus intended to be introduced into the opening of a pulmonary vein. The second end section 9 of the tube 3 with its second end opening 11 protrudes beyond the second end opening 7 of the stent 2. Here, the stent 2 has two opposing (see FIG. 2) wire- or ligature-shaped stabilization elements 12, which also protrude beyond the second end opening 7 of the stent 2 and support the tube 3 from inside. Here, the wire- or ligature-shaped stabilization elements 12 extend essentially up to the second end opening 11 of the tube 3. The wire- or ligature-shaped stabilization elements 12 ensure that the second end opening 11 of the flexible tube 3 remains open in the neutral condition and does not collapse.

Figure 2:
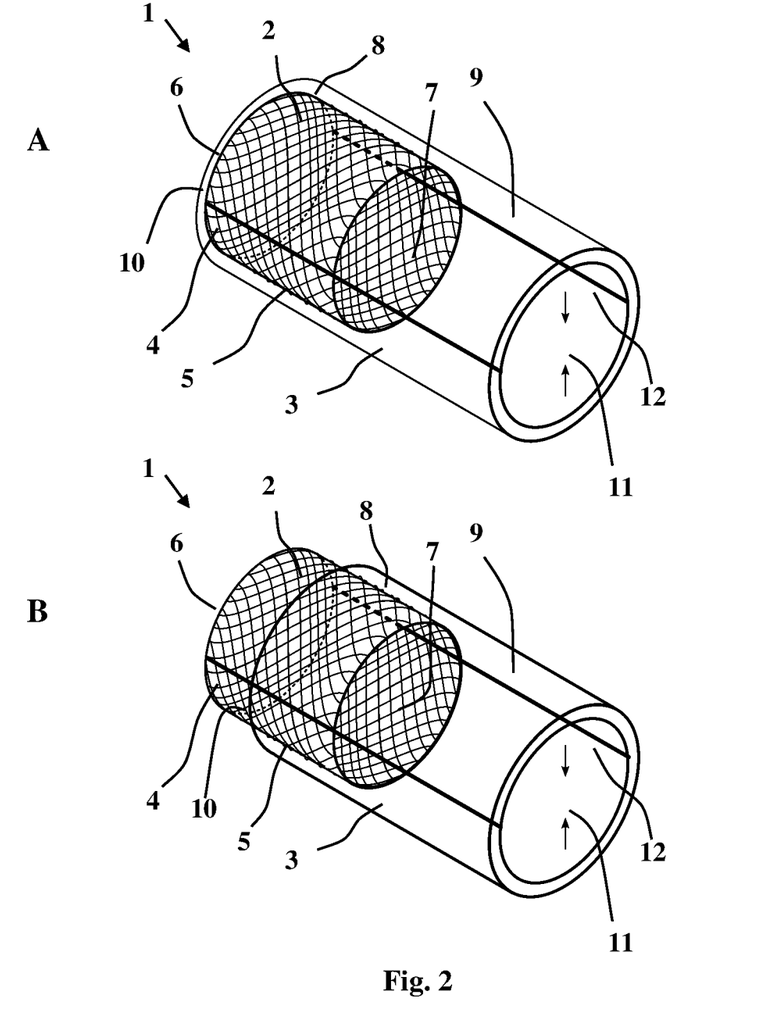
FIG. 2: simplified perspective views of the embodiments of the valve prosthesis in accordance with the invention shown in FIGS. 1A and 1B.

FIG. 2 shows simplified perspective views of the embodiments of the valve prosthesis 1 in accordance with the invention shown in FIG. 1. FIG. 2A shows the embodiment of FIG. 1A again; FIG. 2B shows the embodiment depicted in FIG. 1B. Here, the disposition of the stabilization elements 12 can be seen more easily. Arrows give the direction in which tube walls move when the tube 3 collapses under appropriate pressure conditions.

The two embodiments of the valve prosthesis 1 in accordance with the invention shown in FIGS. 1 and 2 differ only in that the first end section 4 of the stent 2 is either covered by the tube 3 (A) or is exposed (B). In contrast to the embodiment with the covering tube, the embodiment with the exposed first end section 4 results in a reduced reduction in the cross section of the pulmonary vein 31 when the stent 2 is introduced into the pulmonary vein 31 with only the end section 4 not covered by the tube 3.

Figure 3:
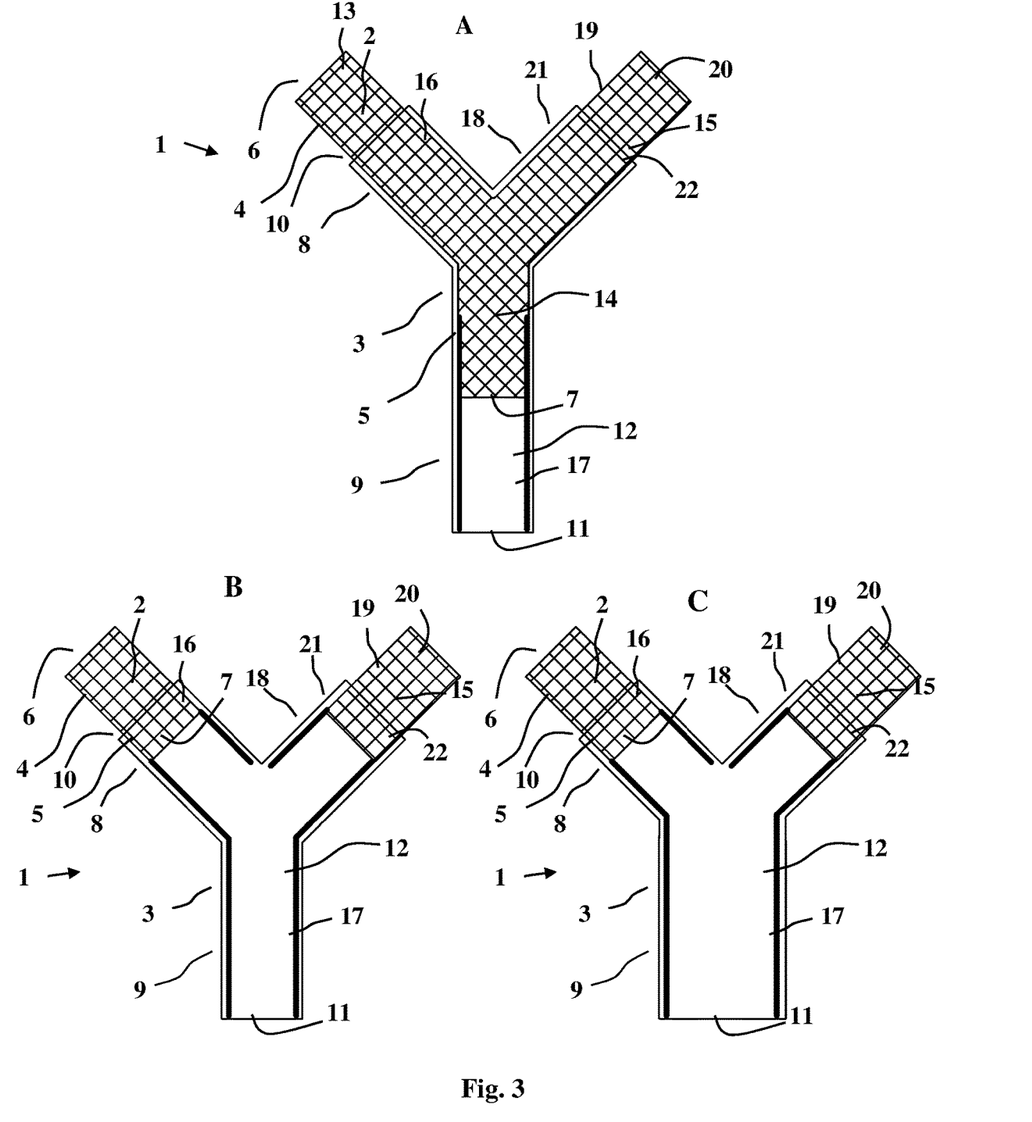
FIGS. 3A-C: views of further embodiments of the valve prosthesis in accordance with the invention.

FIG. 3 diagrammatically shows views of different branched, Y-shaped embodiments of the valve prosthesis 1 in accordance with the invention. In the embodiment shown in FIG. 3A, both the stent 2 and the tube 3 are branched in the shape of a Y, while in the embodiments shown in FIG. 3B and FIG. 3C, only the tube 3 is Y-shaped. The stent 3 of the Y-shaped branched embodiment of the valve prosthesis 1 in accordance with the invention shown in FIG. 3A is divided into a first, second and third leg 13, 14 and 15. Correspondingly, the tube 3 attached to the stent 3 has first, second and third legs 16, 17 and 18. The third leg 15 of the stent 2 has a third end section 19 of the stent 2 with a third end opening 20. Correspondingly, the tube also has a third end section 21 with an end opening 22. Here, the tube 3 is not provided over the entire stent 2, but the first end section 4 on the first leg 13 and the third end section 19 on the third leg 15 of the stent 2 are exposed. These end sections 4, 19 are provided for anchoring in adjacent pulmonary veins 31. The tube 3 with its second end section 9 on the second tube leg 17 and its second end opening 11 protrudes beyond the second end opening 7 of the stent 3 and is supported from inside in its exposed region by opposing wire- or ligature-shaped stabilization elements 12 which are firmly connected to the stent 3.

The embodiments of the valve prosthesis 1 in accordance with the invention shown in FIGS. 3B and 3C are also Y-shaped in configuration. However, here, only the tube 3 is Y-shaped and branched. Hollow cylindrical stents 2 are located in the end sections 8, 21 of the legs 16, 18 of the tube 3, which here are not completely covered by the tube 3, but the end sections 4, 19 are exposed. Stabilization elements 12 are also provided in these embodiments in order to support the tube from inside and to prevent collapse in the neutral state. In the embodiment shown in FIG. 3C, the cross section of the second tube leg 17 is wider compared with the tube cross section in the region of the tube leg 16, 18, in order, when in use, to prevent a limitation of flow of the combined stream of blood from two pulmonary veins 31 in the tube 3.

Figure 4:
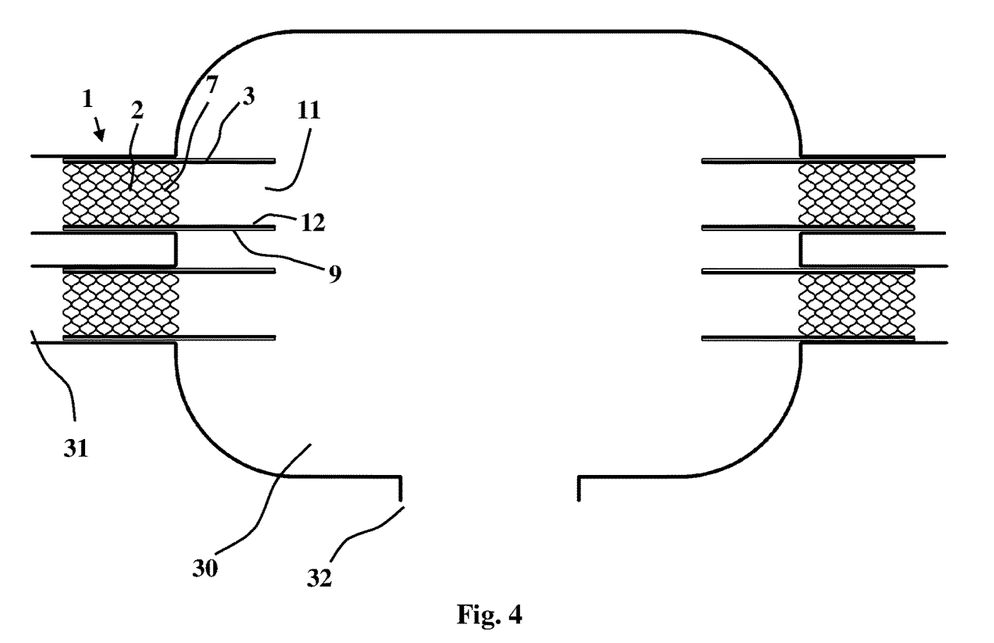
FIG. 4: highly diagrammatic view of a left cardiac atrium with preferred embodiments of the valve prosthesis in accordance with the invention inserted into the openings for the pulmonary vein.

FIG. 4 is a highly diagrammatic illustration of an installation situation. The left cardiac atrium 30 is shown, into which the four pulmonary veins 31 (upper and lower left as well as upper and lower right pulmonary vein) discharge. The mitral valve region as the transition into the left ventricle, not shown here, is indicated solely by an opening 32. Four embodiments of the valve prosthesis 1 in accordance with the invention according to FIGS. 1A and 2A are shown implanted in the opening region of the pulmonary veins 31. For ease of comprehension, not all of the reference numerals are repeated here. The stents 2 here are completely covered by the tube 3 and essentially, their second end openings 7 are flush with the inner wall of the atrium 30. The second tube end sections 9 which protrude beyond the end openings 7 protrude into the atrium 30 and are supported by stabilization elements 12 in a manner such that in the neutral state, their end openings 11 are open. The supply of blood from the pulmonary veins 31 into the atrium 30 is thus not inhibited by the valve prosthesis 1 in accordance with the invention. In the event of reflux of blood from the ventricle into the atrium 30 due to a mitral valve insufficiency, the tube end sections 9 collapse, however, so that the end openings 11 become closed, whereupon a reflux of blood into the pulmonary veins 31 is prevented.

Figure 5:
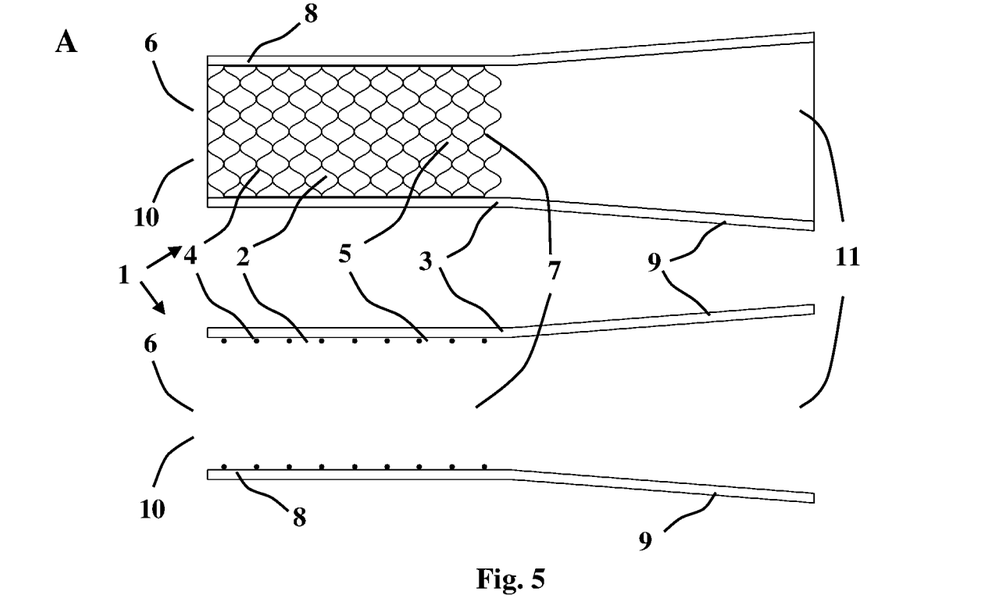
FIGS. 5, 6: two further embodiments (A, B) of the valve prosthesis in accordance with the invention in side views (top) and sectional views (bottom).
Figure 6:
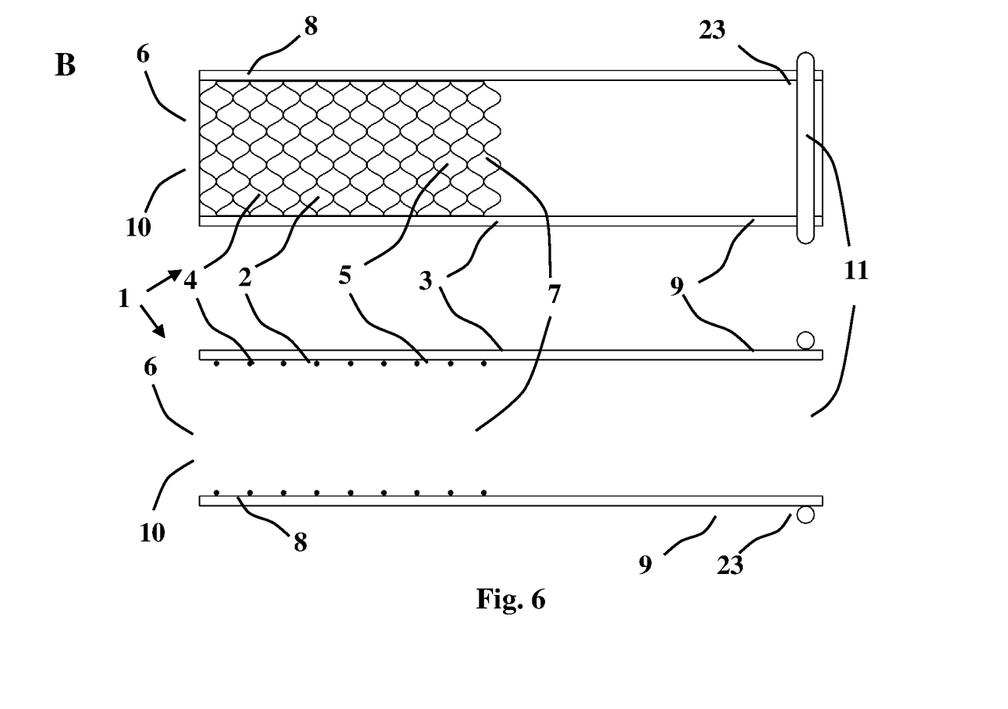

FIGS. 5 and 6 show side views and cross sections through two further embodiments of the valve prosthesis 1 in accordance with the invention. In the embodiment shown in FIG. 5, the cross section of the tube 3 widens conically towards its second end opening 11. Thus, the second end opening is wider than the first end opening 10, whereupon any withdrawal of the tube 3 into the stent 2, for example in an underpressure situation, is prevented. In the embodiment shown in FIG. 6, an annular reinforcing element 23 is provided for this purpose which is disposed on the outside of the tube 3 and acts to stiffen and widen the periphery of the second end section 9 of the tube 3, which also prevents a withdrawal of the tube 3 into the stent 2.

Figure 7:
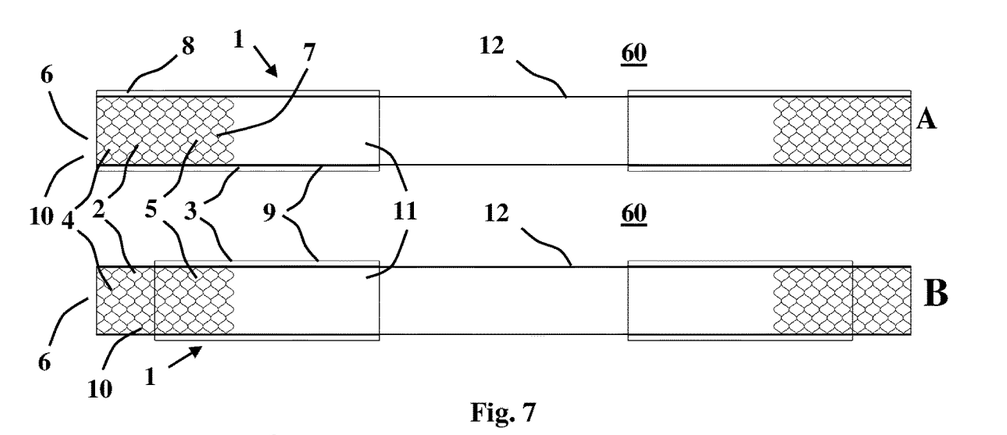
FIG. 7: views of two embodiments (A, B) of the valve prosthesis in accordance with the invention, which is particularly suitable for implantation into the caval veins.
Figure 8:
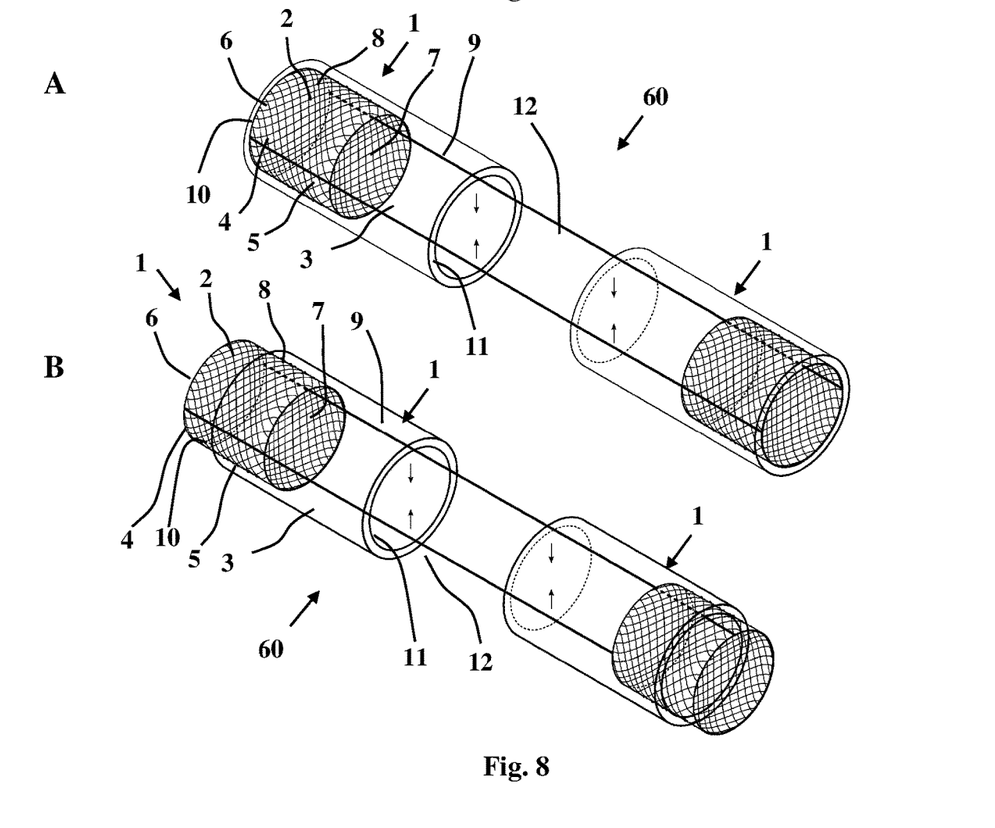
FIG. 8: perspective views of the embodiments of the valve prosthesis in accordance with the invention shown in FIG. 7.

FIGS. 7 and 8 show two embodiments of a valve prosthesis 60 in accordance with the invention which are particularly suitable for use in the caval veins 41, 42. FIG. 7 shows the embodiment in a side view; FIG. 8 shows it in a perspective view. The embodiment shown in FIGS. 7A and 8A differ from the embodiment shown in FIGS. 7B and 8B in that each first end section 4 of the stent 2 is covered by the tube 3, while in the embodiment shown in FIGS. 7B and 8B, each one is exposed.

The embodiments of a valve prosthesis 60 in accordance with the invention shown in FIGS. 7 and 8 respectively consist of two valve prostheses 1 as shown in FIGS. 1 and 2 which are disposed with the second end openings 11 of their tubes 3 orientated towards each other. In this regard, both valve prostheses 1 are spaced from each other so that an open space remains between the end openings 11 of their tubes 3. The open space is bridged by two wire- or ligature-shaped stabilization elements 12 which are configured so as to be connected together or formed together as one piece. In this manner, two valve prostheses 1 are combined to form one valve prosthesis 60 which can be implanted with the respective first end sections 4 of their stent 2 into the upper and lower caval veins 41, 42.

Figure 9:
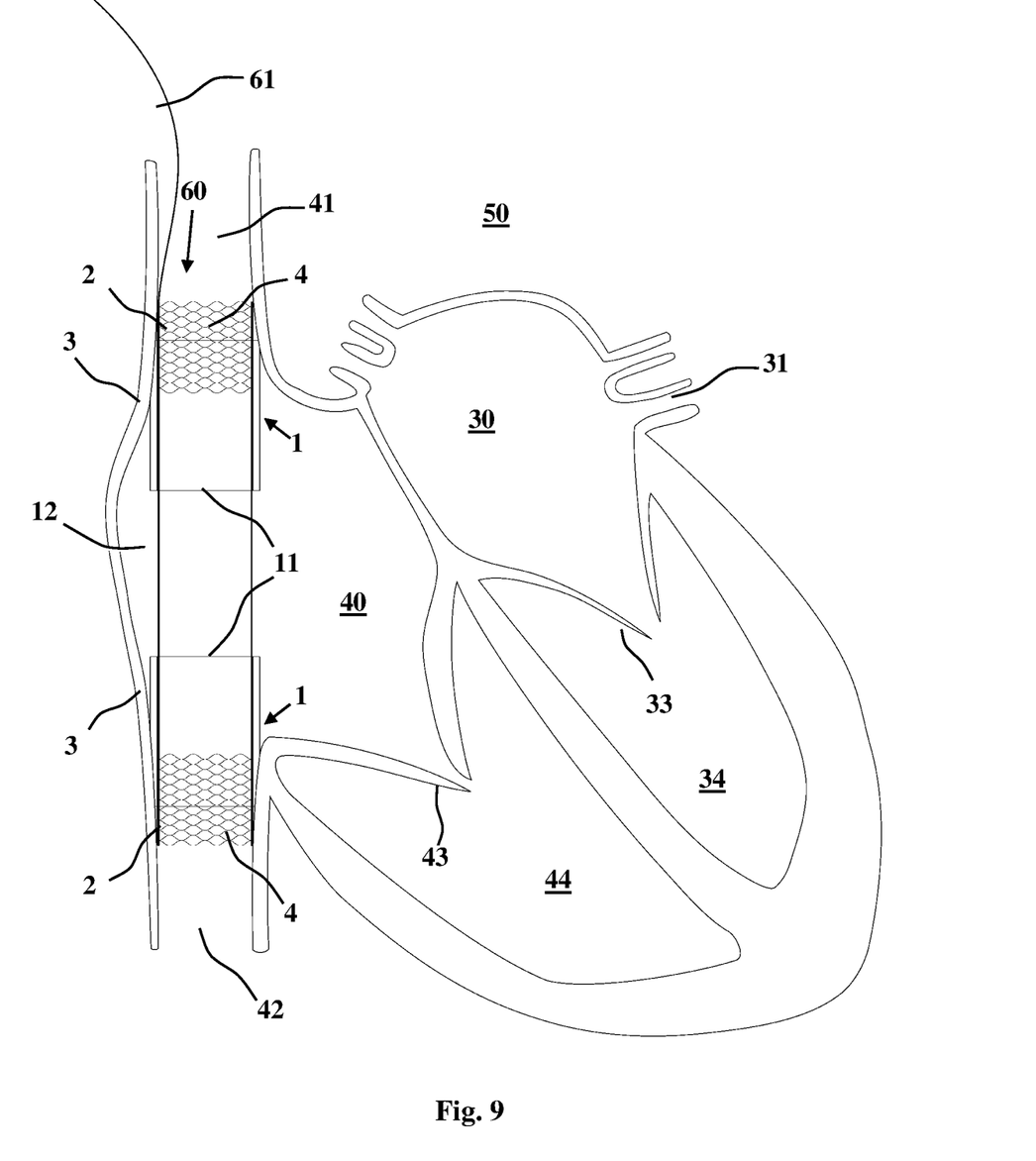
FIG. 9: simplified sectional view through a human heart with an embodiment of the valve prosthesis in accordance with the invention according to FIGS. 7 and 8 implanted into the caval veins.

FIG. 9 shows the embodiment of the valve prosthesis 60 in accordance with the invention shown in FIG. 7B and FIG. 8B when implanted. A diagrammatic cross section through a human heart is shown with the left atrium 30, the left ventricle 34 and the mitral valve 33 between them, as well as the right atrium 40, the right ventricle 44 and the tricuspid valve 43 between them. Pulmonary veins 31 open into the left atrium 30; the upper caval vein 41 and the lower caval vein open into the right atrium 40. The valve prosthesis 60 in accordance with the invention is implanted with the first end section 4 of the first stent 2 into the upper caval vein 41 and with the opposing first end section 4 of the second stent into the lower caval vein 42. In this case, a wire-shaped fastening element 61 is provided for extravasal fastening of the valve prosthesis 60 in accordance with the invention which, for example, is fed in via an implantation vein (for example vena subclavia) and, for example, may be fixed extravasally with surgical suture material.

The second end openings 11 of the valve prosthesis 60 protrude freely into the right atrium 40, but are stabilized by the wire- or ligature-shaped stabilization elements 12. Because of the design of the valve in which the valve prosthesis 60 is open in the neutral state, during physiological flow from the caval veins 41, 42 in the direction of the right atrium 40, no resistance has to be overcome. The flow resistance in the valve prosthesis 60 in accordance with the invention described herein, which may advantageously be used in the case of tricuspid valve insufficiency, is almost negligible. In the case of a non-physiological flow out of the right atrium 40 in the direction of the caval veins 41, 42, the underpressure results in a collapse of the valve prosthesis 1 and thus in an effective closure of the valve. A reverse flow into the caval veins 41, 42 and thus a consequent blood congestion in the liver and kidneys is thus prevented. The valve prosthesis 60 in accordance with the invention may be used completely independently of the pathology and the anatomical characteristics of the tricuspid valve 43.

Figure 10:
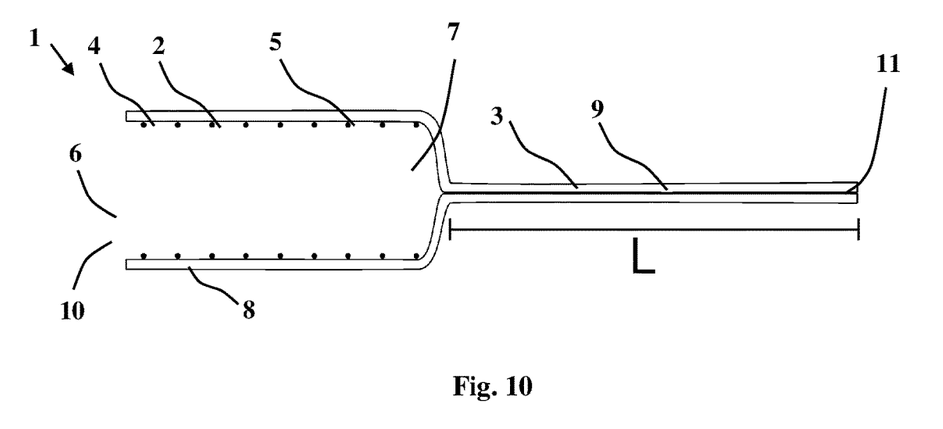
FIG. 10: sectional view of an embodiment of a valve prosthesis in accordance with the invention in the closed state.

FIG. 10 shows a sectional view of an embodiment of a valve prosthesis 1 in accordance with the invention as shown in FIG. 1A, in the closed state, i.e. when the valve is closed. Opposing parts of the region of the tube 3 which protrude beyond the second end opening 7 of the stent 2 lie close together over the coaptation length L so that an effective closure of the valve prosthesis 1 occurs.

EXEMPLARY EMBODIMENT

The functionality of the valve prosthesis 1 in accordance with the invention was determined with the aid of a model set-up. In this regard, an acrylic glass container with two openings was produced. An embodiment of the valve prosthesis 1 in accordance with the invention as shown in FIGS. 1A, 2A was mounted in one of the openings in a manner such that its tube end section 9 protruded freely into the interior of the container. A tube to imitate a pulmonary vein was mounted on the first end section of the stent. Through the second opening, a tube was guided into the container interior through which coloured liquid could be fed from an external container in order to simulate a mitral valve insufficiency. In this manner, an additional rise in pressure occurred in the Plexiglass container. This brought about the collapse of the valve prosthesis in accordance with the invention. By the collapse of the portion of tube protruding into the container, the valve prosthesis 1 in accordance with the invention reliably prevented a reflux of liquid into the tube connected to the valve prosthesis 1.

Furthermore, after the induction of a severe mitral valve insufficiency in the left atrium in pulmonary veins from pig hearts, a valve prosthesis 1 as shown in FIGS. 1A and 2A was implanted and investigated by echocardiography and contrast agent angiography as regards their functionality.

Figure 11:
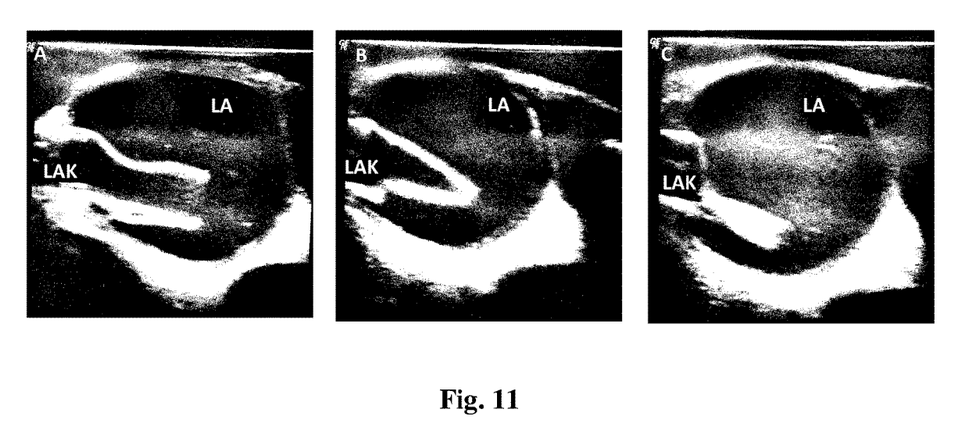
FIG. 11: echocardiogram of a pig heart with a valve prosthesis in accordance with the invention implanted in the left atrium. LA=left atrium, LAK=left atrial valve prosthesis.

FIG. 11 shows an echocardiograph of a pig heart with a valve prosthesis (LAK) implanted in the left atrium. Figure A shows the valve prosthesis 1 in accordance with the invention (LAK) in the open state, Figure B shows it in the closing state and Figure C shows it in the completely closed state. A measurement of the flow rates (not shown) in the valve prosthesis 1 (LAK) and in the left atrium (LA), as expected, produced a unidirectional flow curve for the valve prosthesis 1 and an oscillatory flow in the left atrium.

The invention claimed is:

1. An implantable valve prosthesis (1) adapted for preventing blood reflux from a cardiac atrium into a vein opening into the atrium, comprising
    a generally tubular stent (2) which may be branched or unbranched and which comprises at least a first end section (4) with a first end opening (6) and a second end section (5) with a second end opening (7), and
    a flexible elastic tube (3) which may be branched or unbranched and which has at least a first end section (8) with a first end opening (10) and a second end section (9) with a second end opening (11) and which is disposed at least in a sub-region of the second end section (9) of the stent (2) on the outer peripheral surface thereof in a manner such that the second end section (9) of the flexible elastic tube (3) with its second end opening (11) protrudes beyond the second end opening (7) of the stent (2),
    wherein the flexible elastic tube (3) widens in cross-section towards its second end opening (11) such that the second end opening (11) is wider than the first end opening (10),
    wherein the second end opening (11) of the flexible elastic tube (3) is open in the unpressurized state with no pressure difference between the interior of the tube and the exterior of the tube, and
    wherein the second end opening (11) of the flexible elastic tube (3) is adapted to collapse under pressurized conditions which arise under physiological conditions in a cardiac atrium during systole so that the tube wall of the flexible elastic tube (3) is drawn or pressed towards the interior of the flexible elastic tube (3) and regions of the inner wall of the flexible elastic tube (3) lie on one another and reversibly close the flexible elastic tube (3).

2. The implantable valve prosthesis (1) as claimed in claim 1, further comprising
    at least one wire- or ligature-shaped stabilization element (12) fastened to the stent (2) or integrally formed with the stent (2), wherein the stabilization element (12) protrudes beyond the second end opening (7) of the stent (2) and supports the portion of the tube (3) which protrudes beyond the second end opening (7) of the stent (2) from inside in a manner such that the second end opening (11) of the tube (3) is open in the unpressurized state and cannot gain ingress into the second end opening (7) of the stent (2) when pressure is applied.

3. The implantable valve prosthesis (1) as claimed in claim 2, wherein at least two wire- or ligature-shaped stabilization elements (12) which are opposite each other and which support the tube (3) from inside are present.

4. An implantable valve prosthesis (60), comprising a first and a second implantable valve prosthesis (1) as claimed in claim 2, wherein
    the first and second implantable valve prostheses (1) are disposed opposite one another in a manner such that their second tube end openings (11) are facing each other,
    the second tube end openings (11) of the first and second implantable valve prostheses (1) are spaced from each other,
    the first and second implantable valve prostheses (1) respectively have a wire- or ligature-shaped stabilization element (12) fastened to the stent (2) or integrally formed with the stent (2) which extends beyond the tube end openings (11) of the first and second implantable valve prostheses (1), and
    the first and second implantable valve prostheses (1) are connected together by means of the at least one wire- or ligature-shaped stabilization element (12).

5. The implantable valve prosthesis (60) as in claim 4, wherein the implantable valve prosthesis (1) is adapted for preventing blood reflux from the right cardiac atrium into a caval vein.

6. The implantable valve prosthesis (1) as claimed in claim 1, wherein the stent (2) and the tube (3) are unbranched and generally configured as a hollow cylinder.

7. The implantable valve prosthesis (1) as claimed in claim 1, wherein the tube (3) consists of body tissue.

8. The implantable valve prosthesis (1) as claimed in claim 1, wherein the stent (2) is covered by the tube (3) in the region of its entire outer peripheral surface.

9. The implantable valve prosthesis (1) as claimed in claim 1, wherein the second end section (9) of the tube (3) has an annular reinforcing element (23) fastened to the outside of the tube, the internal cross section of which element (23) corresponding to at least the internal cross section of the second end opening (7) of the stent (2).

10. The implantable valve prosthesis (1) as claimed in claim 1, wherein the implantable valve prosthesis (1) is configured in a manner such that a coaptation length L of at least 1 cm is produced.

11. The implantable valve prosthesis (1) as claimed in claim 1, wherein at least one of the stent (2) and the tube (3) are branched and generally Y-shaped in configuration.

12. The implantable valve prosthesis (1, 60) as claimed in claim 1, wherein the implantable valve prosthesis (1, 60) has a fastening element (61) for extravasal fastening of the implantable valve prosthesis (1, 60).

13. The implantable valve prosthesis (1) as claimed in claim 1, wherein the tube (3) consists of human or animal body tissue.

14. The implantable valve prosthesis (1) as claimed in claim 1, wherein the implantable valve prosthesis (1) is configured in a manner such that a coaptation length L of at least 1.2 cm is produced.

15. The implantable valve prosthesis (1) as claimed in claim 1, wherein the implantable valve prosthesis (1) is configured in a manner such that a coaptation length L of at least 1.3 cm is produced.

16. The implantable valve prosthesis (1) as claimed in claim 1, wherein the implantable valve prosthesis (1) is configured in a manner such that a coaptation length L of at least 1.5 cm is produced.

* * * * *